United States Patent
Voth

(10) Patent No.: US 10,861,246 B2
(45) Date of Patent: Dec. 8, 2020

(54) METHODS AND SYSTEMS FOR GENERATING A PATCH SURFACE MODEL OF A GEOMETRIC STRUCTURE

(71) Applicant: St. Jude Medical, Cardiology Division, Inc., St. Paul, MN (US)

(72) Inventor: Eric J. Voth, Maplewood, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 0 days.

(21) Appl. No.: 15/915,808

(22) Filed: Mar. 8, 2018

(65) Prior Publication Data

US 2018/0240282 A1 Aug. 23, 2018

Related U.S. Application Data

(63) Continuation of application No. 14/887,479, filed on Oct. 20, 2015, now Pat. No. 9,947,142.

(Continued)

(51) Int. Cl.
*G06T 19/20* (2011.01)
*G06T 17/00* (2006.01)
*A61B 34/10* (2016.01)

(52) U.S. Cl.
CPC ............. *G06T 19/20* (2013.01); *G06T 17/00* (2013.01); *A61B 2034/105* (2016.02);
(Continued)

(58) Field of Classification Search
CPC ..... G06T 19/20; G06T 17/00; G06T 2210/44; G06T 2210/56; G06T 2219/2021;
(Continued)

(56) References Cited

U.S. PATENT DOCUMENTS

| | | | | |
|---|---|---|---|---|
| 5,546,327 A | * | 8/1996 | Hattori | G06F 17/5018 |
| | | | | 702/152 |
| 5,601,084 A | * | 2/1997 | Sheehan | B82Y 15/00 |
| | | | | 600/450 |

(Continued)

FOREIGN PATENT DOCUMENTS

| | | | |
|---|---|---|---|
| CN | 103985155 | * | 5/2014 |
| WO | 2014016894 A1 | | 7/2016 |

OTHER PUBLICATIONS

Bagenal, 3D Objecs, URL: http://lasp.colorado.edu/~bagenal/MATH/math4.html (Year: 2014).*

(Continued)

*Primary Examiner* — Phuc N Doan
(74) *Attorney, Agent, or Firm* — Armstrong Teasdale LLP

(57) ABSTRACT

The present disclosure provides systems and methods for generating a patch surface model of a geometric structure. The system includes a computer-based model construction system configured to be coupled to a device that includes at least one sensor configured to acquire a set of original location data points corresponding to respective locations on a surface of the geometric structure, the computer-based model construction system further configured to generate a reference surface based on the acquired original location data points, subdivide the reference surface into a plurality of triangles, project at least some of the original location data points onto a respective nearest point on the subdivided reference surface, compute a function that morphs the projected location data points towards the original location data points to generate a patch surface model, and determine a boundary for the patch surface model.

17 Claims, 10 Drawing Sheets

Related U.S. Application Data

(60) Provisional application No. 62/081,089, filed on Nov. 18, 2014.

(52) U.S. Cl.
CPC ...... *G06T 2210/44* (2013.01); *G06T 2210/56* (2013.01); *G06T 2219/2021* (2013.01)

(58) Field of Classification Search
CPC ......... G06T 7/181; G06T 7/187; G06T 5/001; G06T 5/20; G06T 5/40; G06T 5/50; G06T 7/0083; G06T 11/203; A61B 2019/505; G06K 9/40; G06K 9/38; G06K 9/42; G06K 9/54; G06K 15/02; G09G 5/24; G09G 5/28; G09G 2340/0457
See application file for complete search history.

(56) References Cited

U.S. PATENT DOCUMENTS

| | | | |
|---|---|---|---|
| 6,233,476 B1 | 5/2001 | Strommer et al. | |
| 6,369,815 B1 | 4/2002 | Celniker et al. | |
| 6,498,944 B1 | 12/2002 | Ben-Haim et al. | |
| 6,535,213 B1* | 3/2003 | Ogino | G06T 11/203 345/441 |
| 6,545,676 B1* | 4/2003 | Ryan | G06T 17/20 345/420 |
| 6,591,004 B1 | 7/2003 | Vanessen et al. | |
| 6,690,963 B2 | 2/2004 | Ben-Haim et al. | |
| 6,788,967 B2 | 9/2004 | Ben-Haim et al. | |
| 6,941,251 B1 | 9/2005 | Stallings et al. | |
| 7,197,354 B2 | 3/2007 | Sobe | |
| 7,212,197 B1* | 5/2007 | Schkolne | G06T 19/20 345/419 |
| 7,263,397 B2 | 8/2007 | Hauck et al. | |
| 7,386,339 B2 | 6/2008 | Strommer et al. | |
| 7,936,352 B2 | 5/2011 | Baran et al. | |
| 8,169,435 B2* | 5/2012 | Van Bael | G06T 15/00 345/419 |
| 8,269,770 B1* | 9/2012 | Carr | G06T 17/30 345/419 |
| 8,406,509 B2 | 3/2013 | Okutomi et al. | |
| 2003/0067461 A1* | 4/2003 | Fletcher | G06T 17/20 345/420 |
| 2005/0140670 A1* | 6/2005 | Wu | G06T 15/205 345/419 |
| 2006/0066613 A1 | 3/2006 | Elshishiny | |
| 2007/0225558 A1 | 9/2007 | Hauck et al. | |
| 2010/0054579 A1 | 3/2010 | Okutomi et al. | |
| 2010/0202699 A1* | 8/2010 | Matsuzaka | G06T 11/001 382/195 |
| 2010/0210938 A1 | 8/2010 | Verard et al. | |
| 2011/0316854 A1* | 12/2011 | Vandrovec | G06T 17/005 345/420 |
| 2013/0039578 A1* | 2/2013 | Wang | G01C 11/06 382/173 |
| 2013/0124148 A1 | 5/2013 | Jin et al. | |
| 2013/0185027 A1* | 7/2013 | Lawitschka | A61C 13/0004 703/1 |
| 2013/0249911 A1* | 9/2013 | Mori | G06T 15/005 345/423 |
| 2014/0064625 A1* | 3/2014 | Kim | G06K 9/48 382/203 |
| 2014/0200698 A1* | 7/2014 | Carbonera | G06F 17/50 700/98 |
| 2014/0225888 A1* | 8/2014 | Bell | G06T 17/00 345/419 |
| 2015/0006126 A1 | 1/2015 | Taguchi et al. | |
| 2015/0131914 A1* | 5/2015 | Nakagawa | G06T 19/20 382/203 |

OTHER PUBLICATIONS

Litke, Trimming for Subdivision Surfaces, Elsevier (Year: 2000).*
Bernardini, The ball-pivoting algorithm for surface reconstruction, IEEE Transactions on Visualization and Computer Graphics (vol. 5, Issue: 4, Oct.-Dec. 1999) (Year: 1999).*
Pauly, Point-Based Multiscale Surface Representation, ACM Transactions on Graphics, vol. 25, No. 2, Apr. 2006, pp. 177-193 (Year: 2006).*
Kauffmann, Computer-Aided Method for Quantification of Cartilage Thickness and Volume Changes Using MRI: Validation Study Using a Synthetic Model, IEEE Transactions on Biomedical Engineering, vol. 50, No. 8, Aug. 2003 (Year: 2003).*
Ansys Inc., Manipulating the Boundary Mesh, No. pp. 96 (Year: 2008).*
Bernardini, F., et al. 1999, "The ball-pivoting algorithm for surface reconstruction", IEEE Transactions on Visualization and Computer Graphics 5(4): 349-359.
Richa et al. "Three-dimensional Motion Tracking for Beating Heart Surgery Using a Thin-Plate Spline Deformable Model," The International Journal of Robotics Research, Feb./Mar. 2010, pp. 218-230.
Mcinerney et al. "A Dynamic Finite Element Surface Model for Segmentation and Tracking in Multidimensional Medical Images with Application to Cardiac 4D Image Analysis," Computerized Medical Imaging and Graphics, vol. 19, No. 1, pp. 69-83, 1995.
Hoppe, Surface Reconstruction from Unorganized Points, University of Washington, pp. 8, 1998.
Coelho, Intersecting and Trimming Parametric Meshes, International Journal for Numerical Methods in Engineering, pp. 31, 1998.
Schnabel, Efficient Point-Cloud Processing with Primitive shape, Universität Bonn, Institut für Informatik II, pp. 174, 2009.
Flory, Surface fitting and registration of point clouds using approximations, Computer Aided Geometric Design 27, pp. 60-77, 2010.
Carr, Surface interpolation with radial basis functions for medical imaging, IEEE Trans Med Imaging. Feb. 1997, 16(1): 96-107, pp. 18.
Yeh, Template-based 3D Model Fitting Using Dual-domain Relaxation, IEEE Transactions on Visualization and Computer Graphics, vol. 17 Issue 8, Aug. 2011, pp. 1178-1190, pp. 1-13.
Litke, Trimming for Subdivision Surfaces, Computer Aided Geometric Design archive, vol. 18 Issue 5, Jun. 2001, pp. 463-481, pp. 1-20.
Carr et al., "Reconstruction and representation of 3D objects with radial basis functions", SIGGRAPH, proceedings of the 28th annual conference on computer graphics and interactive techniques, Aug. 2001.
Castellani, Umberto et al., "Joint reconstruction and registration of a deformable planar surface observed by a 3D sensor", 3-D digital imaging and modeling, Aug. 2007.
Chui, Haili et al., "A new point matching algorithm for non-rigid registration", computer vision and image understanding, vol. 89, Issue 2-3, pp. 114-141, Feb. 2003.
Song, Weiwei et al., "Computer-aided modeling and morphological analysis of hip joint", bioinformatics and biomedical engineering, pp. 1218-1221, Jul. 2007.
Japanese-language Notification of Reason for Rejection and corresponding English-language translation, dated Jul. 3, 2018, for related JP patent application No. JP 2017-526064.
Matsuno, Taro, "Computer Simulation of Climate and Earth Simulator," Simulation, Japan, Japan Technical Information Service, Sep. 15, 2001, vol. 20, No. 3, p. 2-6.
Zha, Hongbin, et al., "Shape Description and Modeling of 3D Complex Objects by Using Superquadrics," Material of technical meeting of the Institute of Electrical Engineers of Japan, Japan, Institute of Electrical Engineers of Japan, Dec. 13, 1996, vol. 96-30/43, p. 53-61.

* cited by examiner

METHODS AND SYSTEMS FOR GENERATING A PATCH SURFACE MODEL OF A GEOMETRIC STRUCTURE

CROSS-REFERENCE TO RELATED APPLICATIONS

This application is a continuation of U.S. patent application Ser. No. 14/887,479, filed on Oct. 20, 2015, which claims priority to provisional application Ser. No. 62/081,089, filed Nov. 18, 2014, the entire contents of which are hereby incorporated by reference herein.

FIELD OF THE DISCLOSURE

This disclosure relates to systems and methods for generating a multi-dimensional model of a geometric structure. More particularly, this disclosure relates to computer-implemented systems and methods for generating a patch surface model of a geometric structure, such as, for example, an intra-cardiac structure.

BACKGROUND ART

It is known that various computer-based systems and computer-implemented methodologies can be used to generate multi-dimensional surface models of geometric structures, such as, for example, anatomic structures. More specifically, a variety of systems and methods have been used to generate multi-dimensional surface models of the heart and/or particular portions thereof.

One conventional methodology or technique involves the generation of a plurality of individual surface models corresponding to different regions of interest of a particular structure, and then joining the individual surface models together to form a single composite multi-dimensional surface model. It is known to generate the individual surface models by collecting location data points from the surfaces and volumes enclosed by the surfaces of the respective regions of interest and then using those location data points to generate an individual surface model for each region of interest.

Any number of techniques can be used to generate the individual surface models from the respective location data points, including, for example, convex hull, star-shaped domain approximation, and alpha-shape techniques. However, at least some known modeling systems generate a closed surface, topologically equivalent to a sphere, regardless of the actual geometric structure. Accordingly, if only a portion of a geometric structure is modeled, even if that actual portion is an open surface, at least some known modeling systems will force the generated model to be a closed surface, resulting in an inaccurate pancake-shaped model. Such inaccuracies may impact a user's ability to analyze the geometric structure using the generated model.

BRIEF SUMMARY OF THE DISCLOSURE

In one embodiment, the present disclosure is directed to a system for generating a patch surface model of a geometric structure. The system includes a computer-based model construction system configured to be coupled to a device that includes at least one sensor configured to acquire a set of original location data points corresponding to respective locations on a surface of the geometric structure, the computer-based model construction system further configured to generate a reference surface based on the acquired original location data points, subdivide the reference surface into a plurality of triangles, project at least some of the original location data points onto a respective nearest point on the subdivided reference surface, compute a function that morphs the projected location data points towards the original location data points to generate a patch surface model, and determine a boundary for the patch surface model.

In another embodiment, the present disclosure is directed to a computer-implemented method of generating a patch surface model of a geometric structure. The method includes receiving a set of original location data points corresponding to respective locations on a surface of the geometric structure, generating a reference surface based on the acquired original location data points, subdividing the reference surface into a plurality of triangles, projecting at least some of the original location data points onto a respective nearest point of the subdivided reference surface, computing a function that morphs the projected location data points towards the original location data points to generate a patch surface model, and determining a boundary for the patch surface model.

In another embodiment, the present disclosure is directed to a processing apparatus for generating a patch surface model of a geometric structure. The processing apparatus is configured to receive a set of original location data points corresponding to respective locations on a surface of the geometric structure, generate a reference surface based on the acquired original location data points, subdivide the reference surface into a plurality of triangles, project at least some of the original location data points onto a respective nearest point of the subdivided reference surface, compute a function that morphs the projected location data points towards the original location data points to generate a patch surface model, and determine a boundary for the patch surface model.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The disclosure provides systems and methods for generating a patch surface model (e.g., an interior surface of the heart). The techniques described herein are capable of generating a surface model from a plurality of acquired location data points. As used herein, a "patch surface model" refers to an open or closed surface model that represents any portion (i.e., patch) of an overall surface, including the entire surface. For example, a surface model may include a collection of adjoining triangles modeling part or all of an interior surface of the heart, as described herein.

Figure 1:
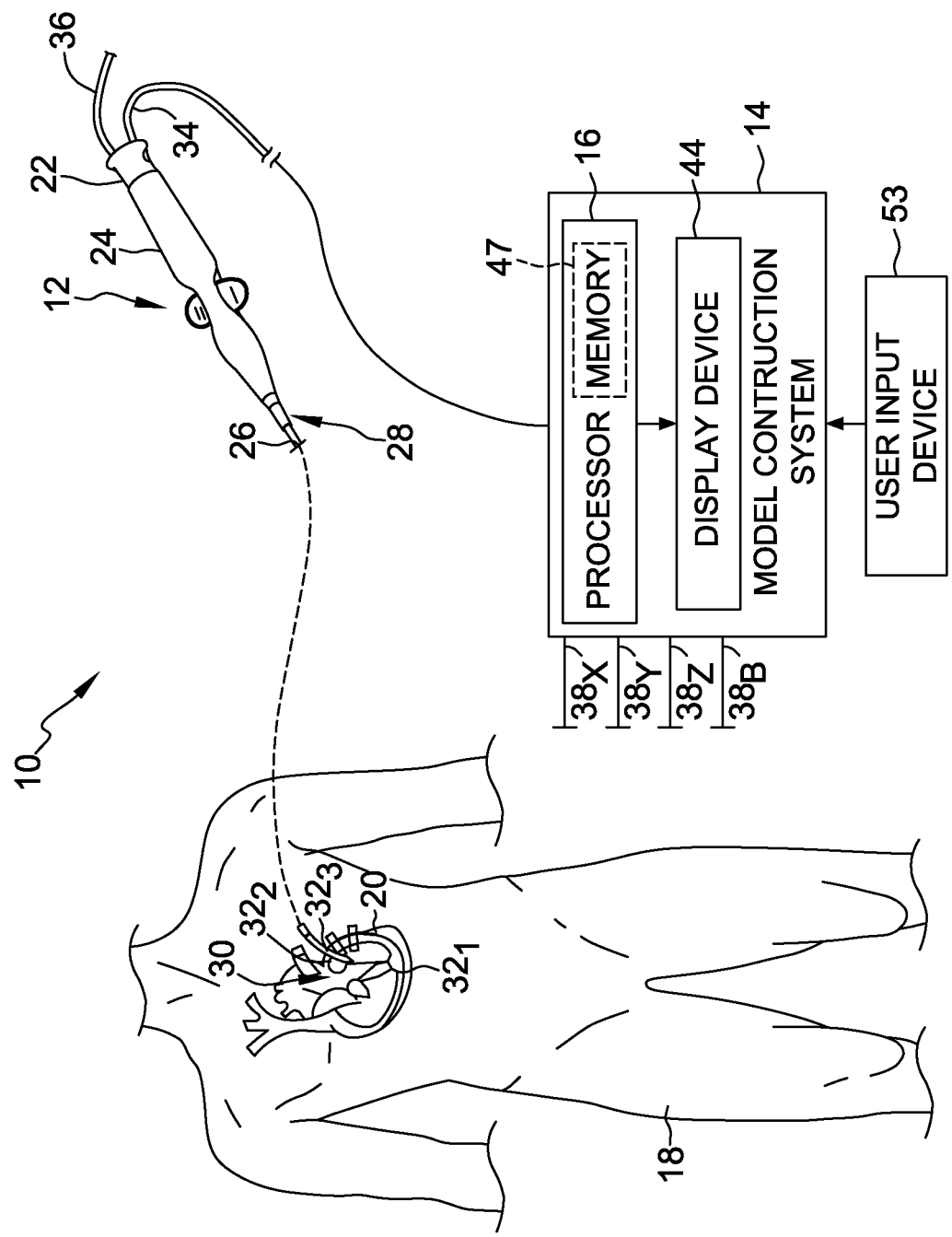
FIG. 1 is a diagrammatic view of a system for generating a multi-dimensional surface model of a geometric structure according to one embodiment.

Referring now to the drawings wherein like reference numerals are used to identify identical components in the various views, FIG. 1 illustrates one exemplary embodiment of a system 10 for generating a multi-dimensional surface model of one or more geometric structures. As will be described below, in this embodiment, the model generated by system 10 is a three-dimensional model. It will be appreciated, however, that while the generation of a three-dimensional model is described below, the present disclosure is not meant to be so limited. Rather, in other embodiments, system 10 may be configured to generate multi-dimensional models other than in three dimensions, and such embodiments remain within the spirit and scope of the present disclosure.

It should be further noted that while the following description focuses primarily on the use of system 10 in the generation of models of anatomic structures, and cardiac structures in particular, the present disclosure is not meant to be so limited. Rather, system 10, and the methods and techniques used thereby, may be applied to the generation of three-dimensional models of any number of geometric structures, including anatomic structures other than cardiac structures. However, for purposes of illustration and ease of description, the description below will be focused on the use of system 10 in the generation of three-dimensional models of cardiac structures.

With continued reference to FIG. 1, in this embodiment, the system 10 includes, among other components, a medical device and a model construction system 14. In this embodiment, medical device is a catheter 12, and model construction system 14 includes, in part, a processing apparatus 16. Processing apparatus 16 may take the form of an electronic control unit, for example, that is configured to construct a three-dimensional model of structures within the heart using data collected by catheter 12.

As illustrated in FIG. 1, catheter 12 is configured to be inserted into a patient's body 18, and more particularly, into the patient's heart 20. Catheter 12 may include a cable connector or interface 22, a handle 24, a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient), and one or more sensors 32 (e.g., $32_1$, $32_2$, $32_3$) mounted in or on shaft 26 of catheter 12. In this embodiment, sensors 32 are disposed at or near distal end 30 of shaft 26. Catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

Connector 22 provides mechanical, fluid, and electrical connection(s) for cables, such as, for example, cables 34, 36 extending to model construction system 14 and/or other components of system 10 (e.g., a visualization, navigation, and/or mapping system (if separate and distinct from model construction system 14), an ablation generator, irrigation source, etc.). Connector 22 is conventional in the art and is disposed at proximal end 28 of catheter 12, and handle 24 thereof, in particular.

Handle 24, which is disposed at proximal end 28 of shaft 26, provides a location for the clinician to hold catheter 12 and may further provide means for steering or guiding shaft 26 within body 18 of the patient. For example, handle 24 may include means to change the length of a steering wire extending through catheter 12 to distal end 30 of shaft 26 to steer shaft 26. Handle 24 is also conventional in the art and it will be understood that the construction of handle 24 may vary. In other embodiments, catheter 12 may be robotically driven or controlled. Accordingly, rather than a clinician manipulating a handle to steer or guide catheter 12 and shaft 26 thereof, in such an embodiments, a robot is used to manipulate catheter 12.

Shaft 26 is an elongate, tubular, flexible member configured for movement within body 18. Shaft 26 supports, for example and without limitation, sensors and/or electrodes mounted thereon, such as, for example, sensors 32, associated conductors, and possibly additional electronics used for signal processing and conditioning. Shaft 26 may also permit transport, delivery, and/or removal of fluids (including irrigation fluids, cryogenic ablation fluids, and bodily fluids), medicines, and/or surgical tools or instruments. Shaft 26 may be made from conventional materials such as polyurethane, and defines one or more lumens configured to house and/or transport electrical conductors, fluids, or surgical tools. Shaft 26 may be introduced into a blood vessel or other structure within the body 18 through a conventional introducer. Shaft 26 may then be steered or guided through body 18 to a desired location, such as heart 20, using means well known in the art.

Sensors 32 mounted in or on shaft 26 of catheter 12 may be provided for a variety of diagnostic and therapeutic purposes including, for example and without limitation, electrophysiological studies, pacing, cardiac mapping, and ablation. In this embodiment, one or more of sensors 32 are provided to perform a location or position sensing function. More particularly, and as will be described in greater detail below, one or more of sensors 32 are configured to be a positioning sensor(s) that provides information relating to the location (position and orientation) of catheter 12, and distal end 30 of shaft 26 thereof, in particular, at certain points in time. Accordingly, as catheter 12 is moved along a surface of a structure of interest of heart 20 and/or about the interior of the structure, sensor(s) 32 can be used to collect location data points that correspond to the surface of, and/or other locations within, the structure of interest. These location data points can then be used by, for example, model construction system 14, in the construction of a three-dimensional model of the structure of interest, which will be described in greater detail below. For purposes of clarity and illustration, the description below will discuss an embodiment wherein multiple sensors 32 of catheter 12 comprise positioning sensors. It will be appreciated, however, that in other embodiments, which remain within the spirit and scope of the present disclosure, catheter 12 may comprise both one or more positioning sensors as well as other sensors configured to perform other diagnostic and/or therapeutic functions.

As briefly described above, and as will be described in greater detail below, model construction system 14 is configured to construct a three-dimensional model of structures within the heart using, in part, location data collected by catheter 12. More particularly, processing apparatus 16 of model construction system 14 is configured to acquire location data points collected by sensor(s) 32 and to then use those location data points in the construction or generation of a model of the structure(s) to which the location data points correspond. In this embodiment, model construction system 14 acquires the location data points by functioning with sensors 32 to collect location data points. In other embodiments, however, model construction system 14 may simply acquire the location data points from sensors 32 or another component in system 10, such as, for example, a memory or other storage device that is part of model construction system 14 or accessible thereby, without affirmatively taking part in the collection of the location data points. Model construction system 14 is configured to construct a three-dimensional model based on some or all of the collected location data points. For purposes of illustration and clarity, the description below will be limited to an embodiment wherein model construction system 14 is configured to both construct the model and also acquire location data points by functioning with sensor(s) 32 in the collection of the location data points. It will be appreciated, however, that other embodiments wherein model construction system 14 only acquires location data points from sensor(s) 32 or another component of system 10 and then constructs a three-dimensional model based thereon remain within the spirit and scope of the present disclosure.

Accordingly, in this embodiment, in addition to constructing a model of a structure, model construction system 14 is configured to function with sensor(s) 32 to collect location data points that are used in the construction of a three-dimensional model. Model construction system 14 may comprise an electric field-based system, such as, for example, the EnSite™ NavX™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other embodiments, however, model construction system 14 may comprise other types of systems, such as, for example and without limitation: a magnetic-field based system such as the Carto™ system available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster; as well as other impedance-based localization systems, acoustic or ultrasound-based systems, and commonly available fluoroscopic, computed tomography (CT), and magnetic resonance imaging (MRI)-based systems.

As briefly described above, sensor(s) 32 of catheter 12 include positioning sensors. Sensor(s) 32 produce signals indicative of catheter location (position and/or orientation) information. In this embodiment, wherein model construction system 14 is an electric field-based system, sensor(s) 32 may comprise one or more electrodes. Alternatively, in an embodiment where model construction system 14 is a magnetic field-based system, sensor(s) 32 may include one or more magnetic sensors configured to detect one or more characteristics of a low-strength magnetic field. For instance, in one exemplary embodiment, sensor(s) 32 may include magnetic coils disposed on or in shaft 26 of catheter 12.

For purposes of clarity and illustration, model construction system 14 will hereinafter be described as including an electric field-based system, such as, for example, the EnSite™ NavX™ system identified above. It will be appreciated that while the description below is primarily limited to an embodiment wherein sensor(s) 32 include one or more electrodes, in other embodiments, sensor(s) 32 may include one or more magnetic field sensors (e.g., coils). Accordingly, model construction systems that include positioning sensor(s) other than the sensors or electrodes described below remain within the spirit and scope of the present disclosure.

Figure 2:
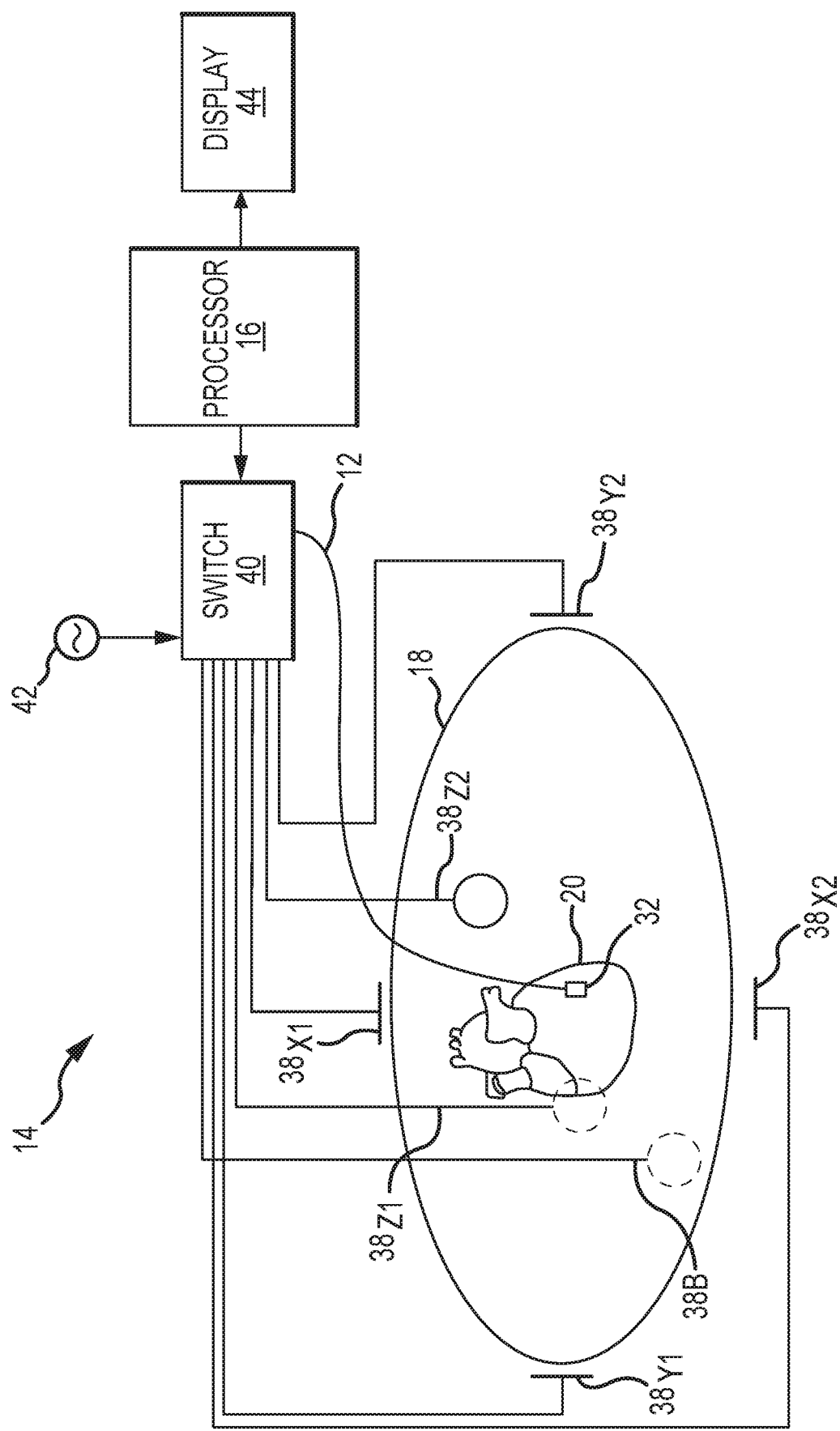
FIG. 2 is a diagrammatic and schematic view of a model construction system of the system illustrated in FIG. 1.

With reference to FIG. 2, in addition to the processing apparatus 16, model construction system 14 may include, among other possible components, a plurality of patch electrodes 38, a multiplex switch 40, a signal generator 42, and a display device 44. In other embodiments, some or all of these components are separate and distinct from model construction system 14 but are electrically connected to, and configured for communication with, model construction system 14.

Processing apparatus 16 may include a programmable microprocessor or microcontroller, or may include an application specific integrated circuit (ASIC). Processing apparatus 16 may include a central processing unit (CPU) and an input/output (I/O) interface through which the processing apparatus 16 may receive a plurality of input signals including, for example, signals generated by patch electrodes 38 and sensor(s) 32, and generate a plurality of output signals including, for example, those used to control and/or provide data to, for example, display device 44 and switch 40. Processing apparatus 16 may be configured to perform various functions, such as those described in greater detail above and below, with appropriate programming instructions or code (i.e., software). Accordingly, processing apparatus 16 is programmed with one or more computer programs encoded on a computer storage medium for performing the functionality described herein.

With the possible exception of patch electrode $38_B$ called a "belly patch," patch electrodes 38 are provided to generate electrical signals used, for example, in determining the position and orientation of catheter 12. In one embodiment, patch electrodes 38 are placed orthogonally on the surface of body 18 and are used to create axes-specific electric fields within body 18. For instance, in one embodiment, patch electrodes $38_{X1}$, $38_{X2}$ may be placed along a first (x) axis. Patch electrodes $38_{Y1}$, $38_{Y2}$ may be placed along a second (y) axis, and patch electrodes $38_{Z1}$, $38_{Z2}$ may be placed along a third (z) axis. Each of patch electrodes 38 may be coupled to multiplex switch 40. In this embodiment, processing apparatus 16 is configured, through appropriate software, to provide control signals to switch 40 to thereby sequentially couple pairs of electrodes 38 to signal generator 42. Excitation of each pair of electrodes 38 generates an electric field within body 18 and within an area of interest such as heart 20. Voltage levels at non-excited electrodes 38, which are referenced to belly patch $38_B$, are filtered and converted and provided to processing apparatus 16 for use as reference values.

In this embodiment, sensor(s) 32 of catheter 12 are electrically coupled to processing apparatus 16 and are configured to serve a position sensing function. More particularly, sensor(s) 32 are placed within electric fields created in body 18 (e.g., within the heart) by exciting patch electrodes 38. For purposes of clarity and illustration only, the description below will be limited to an embodiment wherein a single sensor 32 is placed within electric fields. It will be appreciated, however, that in other embodiments that remain within the spirit and scope of the present disclosure, a plurality of sensors 32 can be placed within the electric fields and then positions and orientations of each sensor can be determined using the techniques described below.

When disposed within the electric fields, sensor 32 experiences voltages that are dependent on the location between patch electrodes 38 and the position of sensor 32 relative to tissue. Voltage measurement comparisons made between sensor 32 and patch electrodes 38 can be used to determine the location of sensor 32 relative to the tissue. Accordingly, as catheter 12 is swept about or along a particular area or surface of interest, processing apparatus 16 receives signals (location information) from sensor 32 reflecting changes in voltage levels on sensor 32 and from the non-energized patch electrodes 38. Using various known algorithms, the processing apparatus 16 may then determine the location (position and orientation) of sensor 32 and record it as a location data point 46 (also referred to herein as "data point 46" and illustrated in FIG. 3) corresponding to a location of sensor 32, and therefore, a point on the surface or in the interior of the structure of interest being modeled, in a memory or storage device, such as memory 47, associated with or accessible by processing apparatus 16. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Further, locations of other portions of catheter 12 may be inferred from measurements at sensors 32, such as by interpolation or extrapolation, to generate further location data points 46. In any event, the collection of location data points 46 ($46_1$, $46_2$, . . . , $46_n$) taken over time results in the formation of a point cloud 48 (best shown in FIG. 3) stored in the memory or storage device.

While the description above has thus far been generally with respect to an orthogonal arrangement of patch electrodes 38, the present disclosure is not meant to be so limited. Rather, in other embodiments, non-orthogonal arrangements may be used to determine the location coordinates of sensor 32. For example, and in general terms, FIGS. 4A-4D depict a plurality of exemplary non-orthogonal dipoles $D_0$, $D_1$, $D_2$, and $D_3$, set in a coordinate system 50. In FIGS. 4A-4D, the X-axis patch electrodes are designated $X_A$ and $X_B$, the Y-axis patch electrodes are designated $Y_A$ and $Y_B$, and the Z-axis patch electrodes are designated $Z_A$ and $Z_B$. For any desired axis, the potentials measured across an intra-cardiac sensor, such as sensor 32, resulting from a predetermined set of drive (source sink) configurations may be combined algebraically to yield the same effective potential as would be obtained simply by driving a uniform current along the orthogonal axes. Any two of the patch electrodes $38_{X1}$, $38_{X2}$, $38_{Y1}$, $38_{Y2}$, $38_{Z1}$, and $38_{Z2}$ (See FIG. 2) may be selected as a dipole source and drain with respect to a ground reference, e.g., belly patch $38_B$, while the unexcited patch electrodes measure voltage with respect to the ground reference. Sensor 32 placed in heart 20 is also exposed to the field for a current pulse and is measured with respect to ground (e.g., belly patch $38_B$).

In another exemplary embodiment, multiple patch electrodes 38 may be arranged linearly along a common axis. In such an embodiment, excitation of an electrode pair comprising one of patch electrodes 38 and an electrode mounted on catheter 12 generates an electric field. The non-excited patch electrodes 38 may then measure potentials that can be used to determine the position of sensor 32. Accordingly, in such an embodiment, the excitation of multiple electrode pairs comprising different patch electrodes 38 and the catheter-mounted electrode may be used to determine the position of sensor 32.

Data sets from each of patch electrodes 38 and the sensor 32 are all used to determine the location of sensor 32 within heart 20. After the voltage measurements are made, a different pair of patch electrodes 38 is excited by the current source and the voltage measurement process of the remaining patch electrodes 38 and sensor 32 takes place. Once the location of sensor 32 is determined, and as was described above, the location may be recorded as a data point 46 in the same manner described above. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Accordingly, it will be appreciated that any number of techniques may be used to determine locations of sensor 32 and to, therefore, collect data points corresponding thereto, each of which remains within the spirit and scope of the present disclosure.

Figure 3:
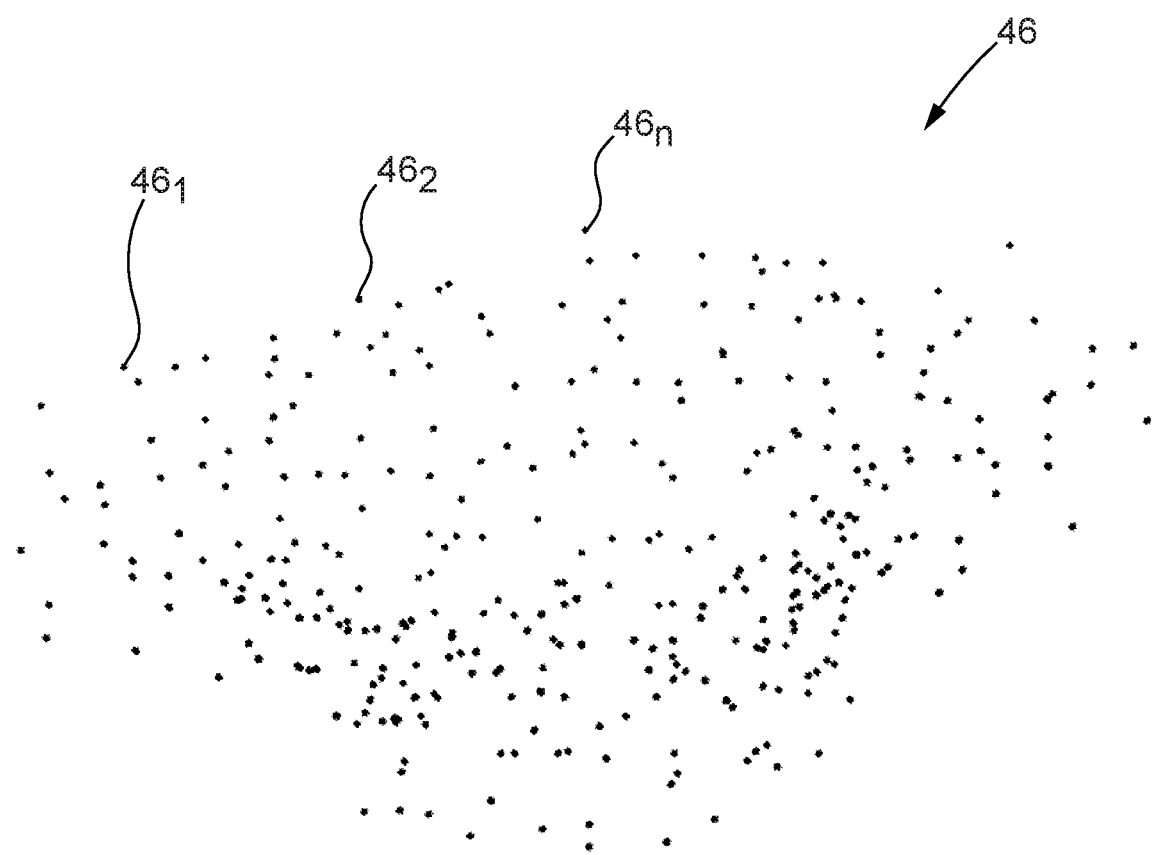
FIG. 3 is a schematic view of a point cloud containing a collection of location data points.
Figure 4A:
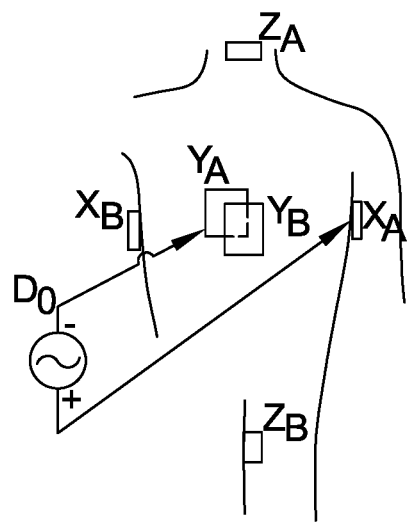
FIGS. 4A-4D are schematic diagrams of exemplary dipole pairs of driven patch electrodes suitable for use in the model construction system illustrated in FIG. 2.
Figure 4B:
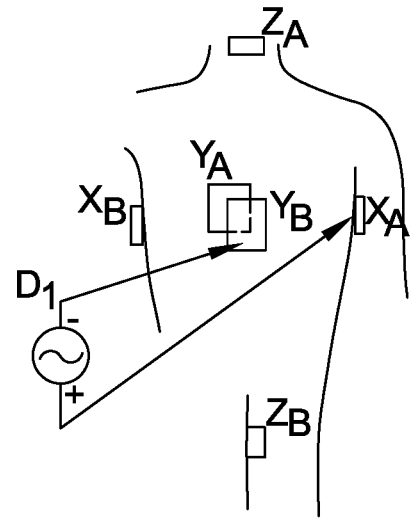
Figure 4C:
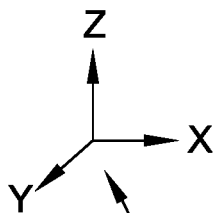
Figure 4C:
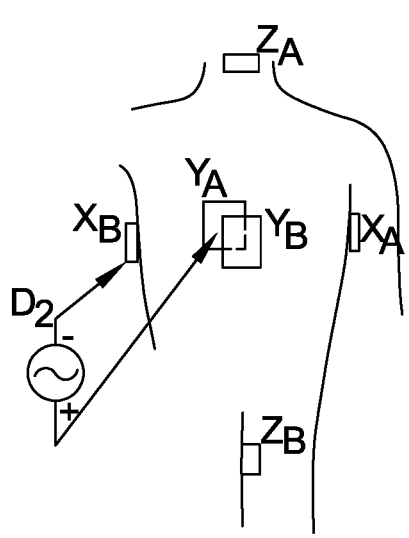
Figure 4D:
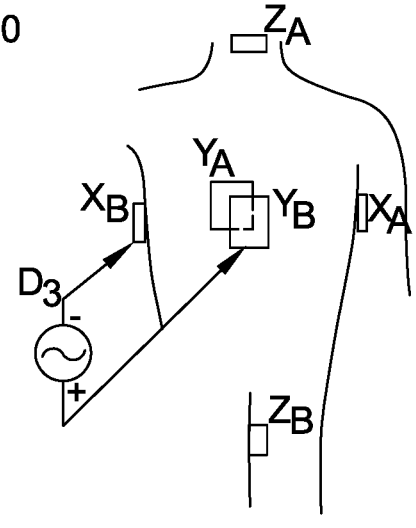

FIG. 3 is illustrative of the point cloud 48 including location data points $46_1$, $46_2$, . . . $46_n$ corresponding to a particular structure of interest being modeled. It will be appreciated that in practice, the point cloud 48 would generally include hundreds to hundreds of thousands of data points 46. For purposes of illustration and ease of description, however, the description below will be limited to a point cloud having a limited number of location data points, such as, for example, point cloud 48 including location data points 46. It will be further appreciated that location data points 46 corresponding to different regions of the structure of interest may be collected. In such an embodiment, processing apparatus 16 may be configured to group data points 46 corresponding to the region of the structure of interest from which they were collected. As such, if there are two regions of the structure of interest, all of the location data points corresponding to a first region will be grouped together and form a first point cloud, while all of the data points corresponding to a second region will be likewise grouped together and form a second point cloud.

Figure 5:
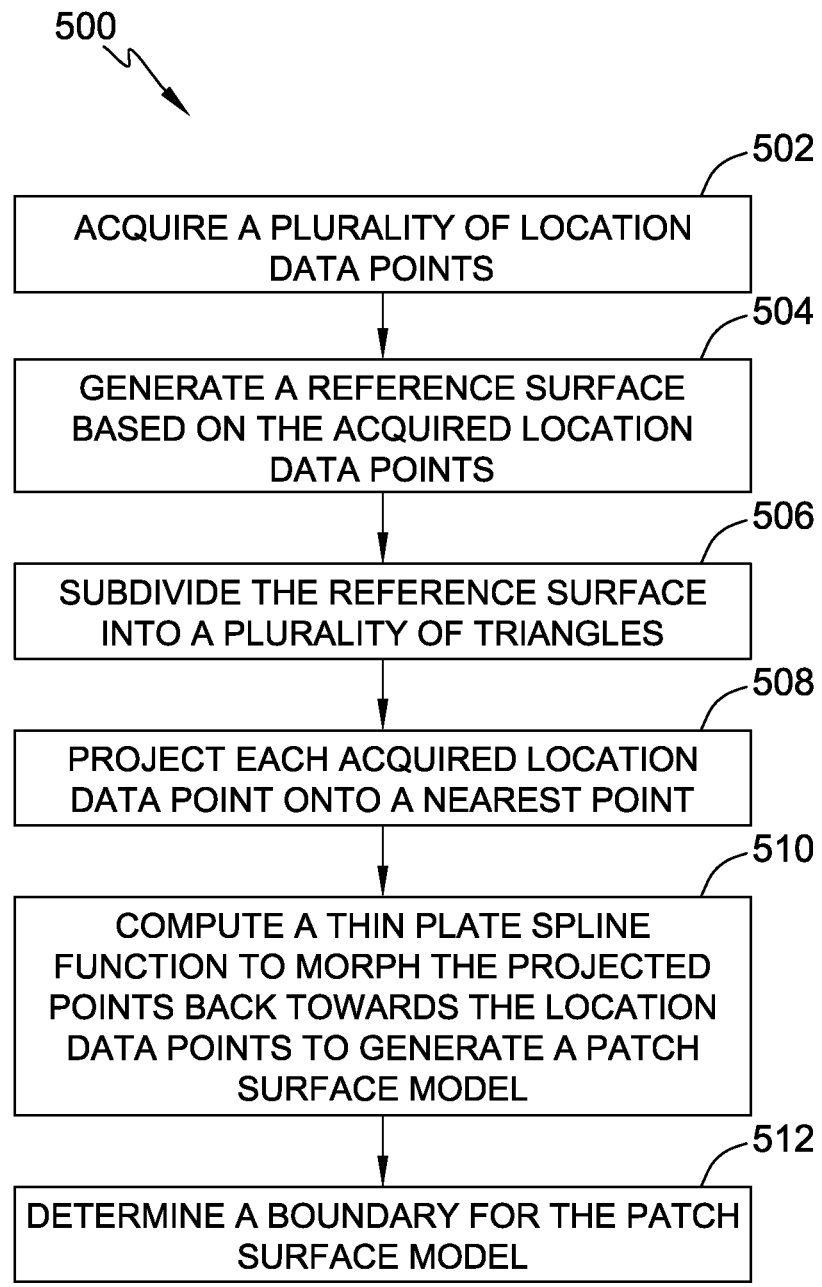
FIG. 5 is a flow diagram illustrating a method of generating a patch surface model according to one embodiment.

FIG. 5 is a flow diagram of a method 500 for generating a patch surface model. In some embodiments, for example, method 500 is performed using processing apparatus 16 described above. Method 500 includes acquiring 502 a plurality of location data points, such as location data points 46 (shown in FIG. 3). Location data points may be acquired 502, for example, using the systems and methods described above.

A reference surface is generated 504 based on the location data points. Specifically, a reference surface that best approximates the point cloud formed by location data points is generated. In some embodiments, depending on the overall shape of the point cloud, the reference surface is a plane or a sphere. Alternatively, the reference surface may be any geometric shape that enables method 500 to function as described herein. In one embodiment, a sphere that best fits the point cloud is initially chosen. If the radius of the chosen sphere is so large (e.g., larger than 200 millimeters (mm)) that subdividing it (as described below) would be impractical (e.g., because it would require so many vertices and triangles to get a triangle size small enough to display the geometry and map in sufficient detail), the point cloud is best-fit to a plane instead.

The reference surface is subdivided 506 into a plurality of triangles. In one embodiment, the references surface is subdivided 506 into equilateral triangles, each equilateral triangle having three vertices. The size of the equilateral triangles may be specified by a user operating, for example, user input device 53 (shown in FIG. 1). Smaller equilateral triangles will result in more vertices, and larger equilateral triangles will result in fewer vertices.

Figure 6A:
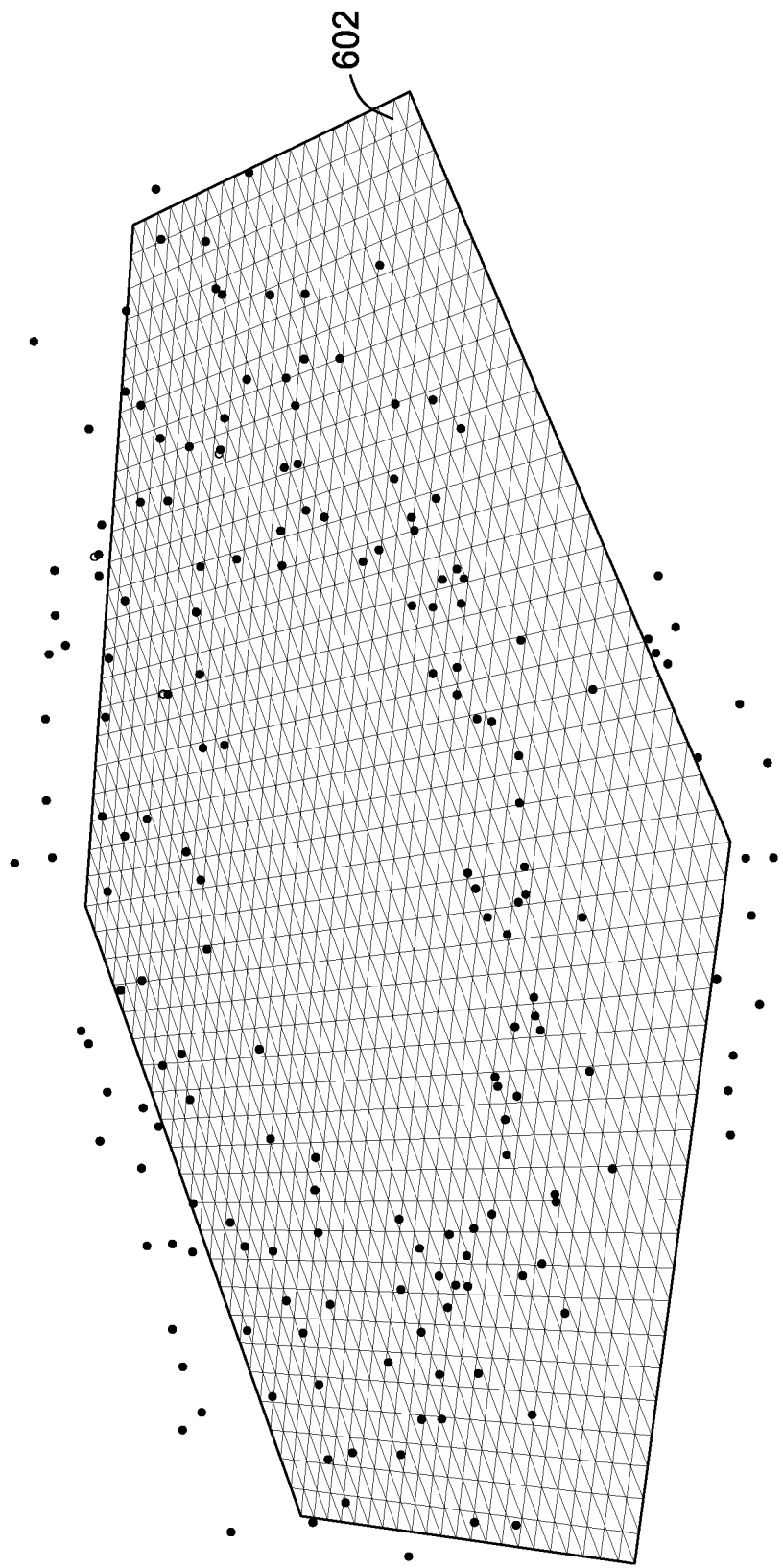
FIG. 6A is a schematic view of a subdivided planar reference surface generated for the point cloud illustrated in FIG. 3.
Figure 6B:
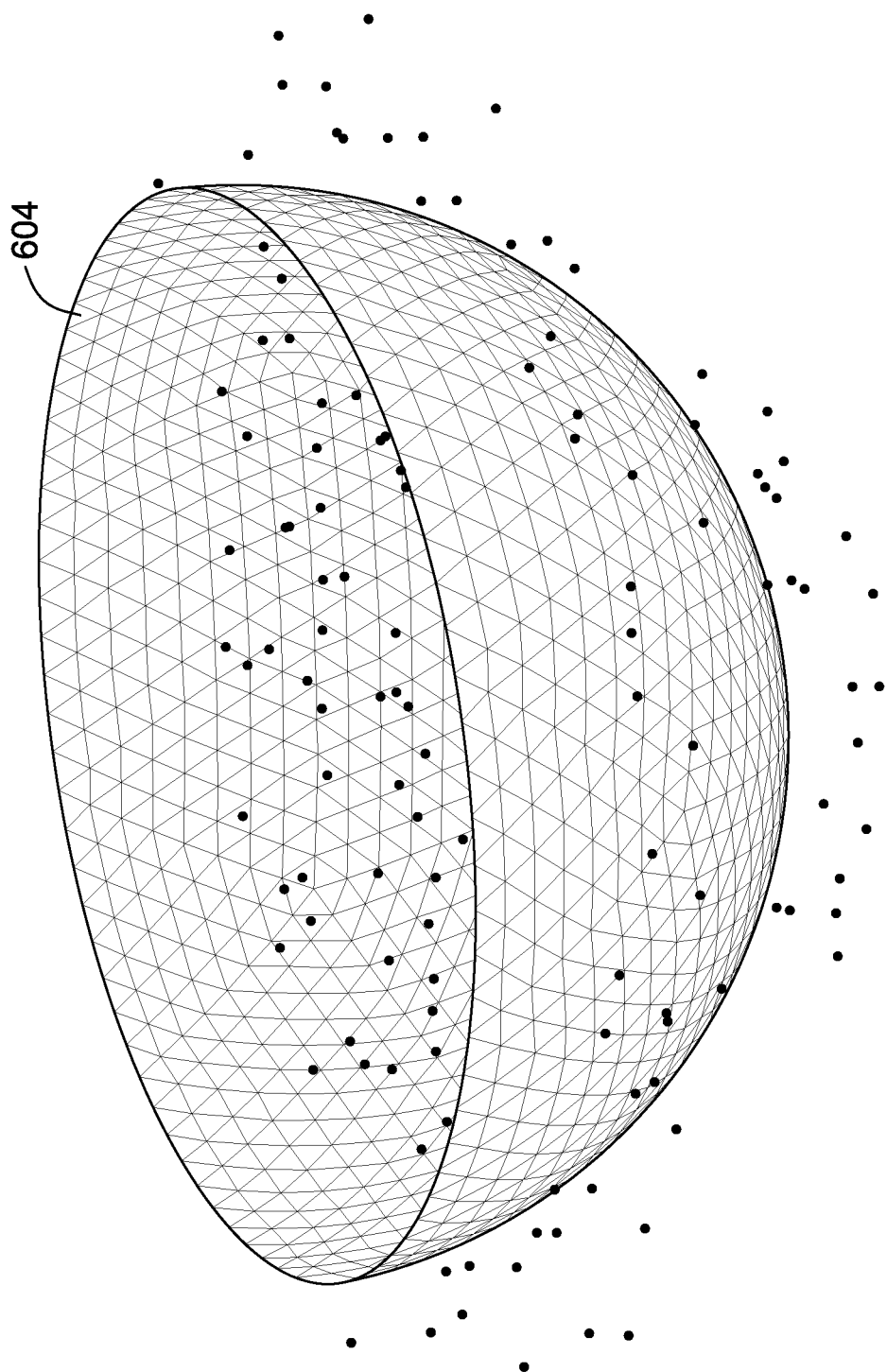
FIG. 6B is a schematic view of a subdivided spherical reference surface generated for the point cloud illustrated in FIG. 3.

When the reference surface is a plane, dividing the plane into a plurality of equilateral triangles is relatively straightforward. When the reference surface is a sphere, the sphere may be decimated into an icosahedron (i.e., a polyhedron with twenty faces). Each face of the icosahedron is an equilateral triangle with three vertices. Further, each face can be recursively split into smaller triangles until the triangles reach the predetermined size. FIG. 6A shows a subdivided planar reference surface 602 generated for point cloud 48 (shown in FIG. 3), and FIG. 6B shows a subdivided spherical reference surface 604 generated for point cloud 48.

With the triangles of the reference surface identified, in this embodiment, each location data point in the point cloud is projected 508 onto a nearest point on the reference surface. Alternatively, in some embodiments, only a subset (i.e., less than all) of the location data points are projected onto a nearest point on the reference surface. This improves the real-time performance of method 500. For example, in one embodiment, a predetermined number of location data points (e.g., 800 points) are projected. To determine the points, the entire 3D space of the geometry may be divided into multiple bins (e.g., voxels), and each of the original location data points are associated with the bin in which they lie. The number of bins, N, that include location data points is counted. If N is less than half the predetermined number (e.g., less than 400 points), the bins are made smaller. If N is greater than the limit, the bins are made larger. Then, one random location data point is chosen from each bin, and the chosen point is projected onto the reference surface. This provides a more uniform distribution than if 800 points were randomly chosen over the entire 3D space.

Figure 7A:
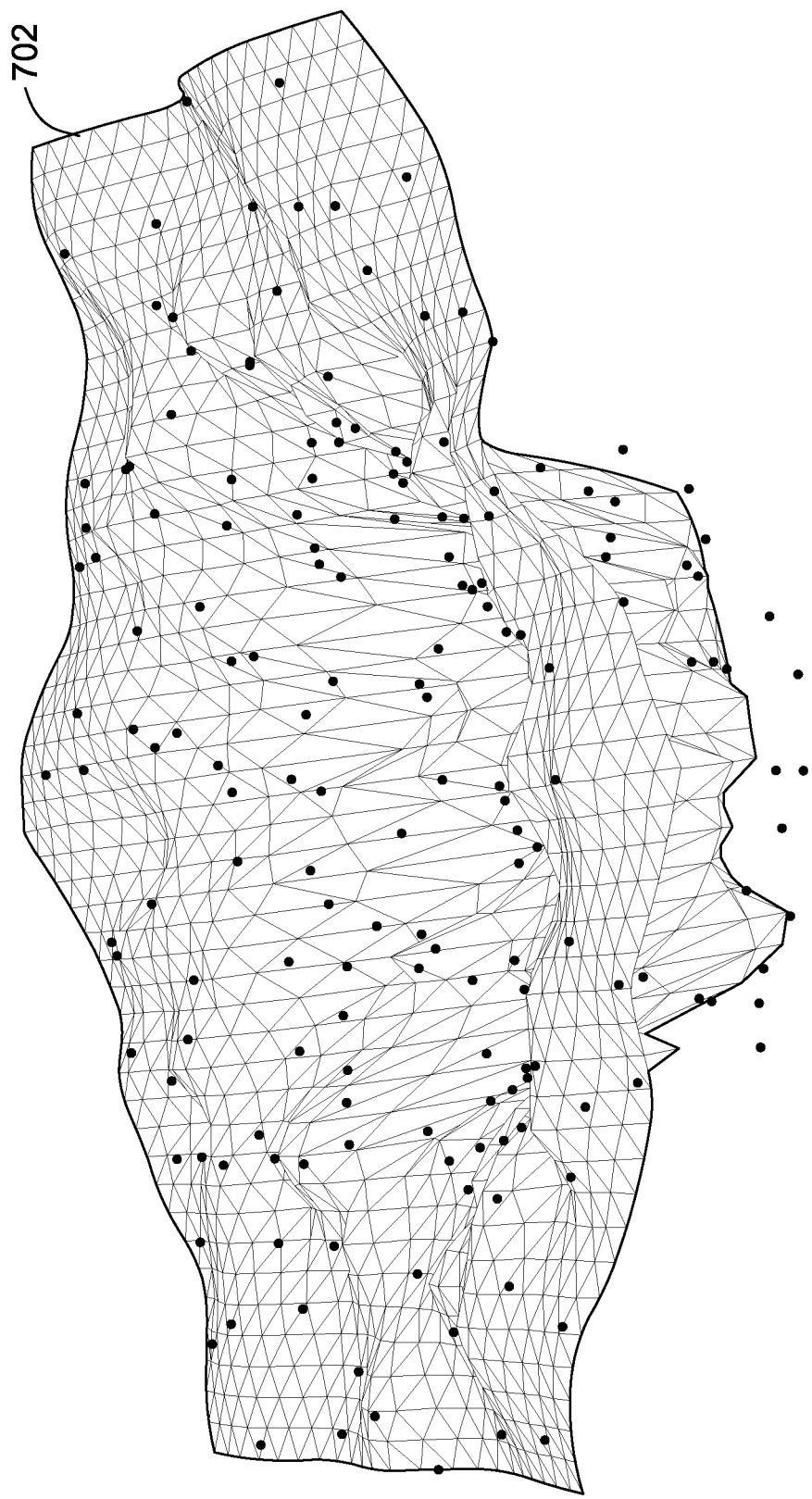
FIG. 7A is a schematic view of a patch surface model generated from the subdivided planar reference surface illustrated in FIG. 6A.
Figure 7B:
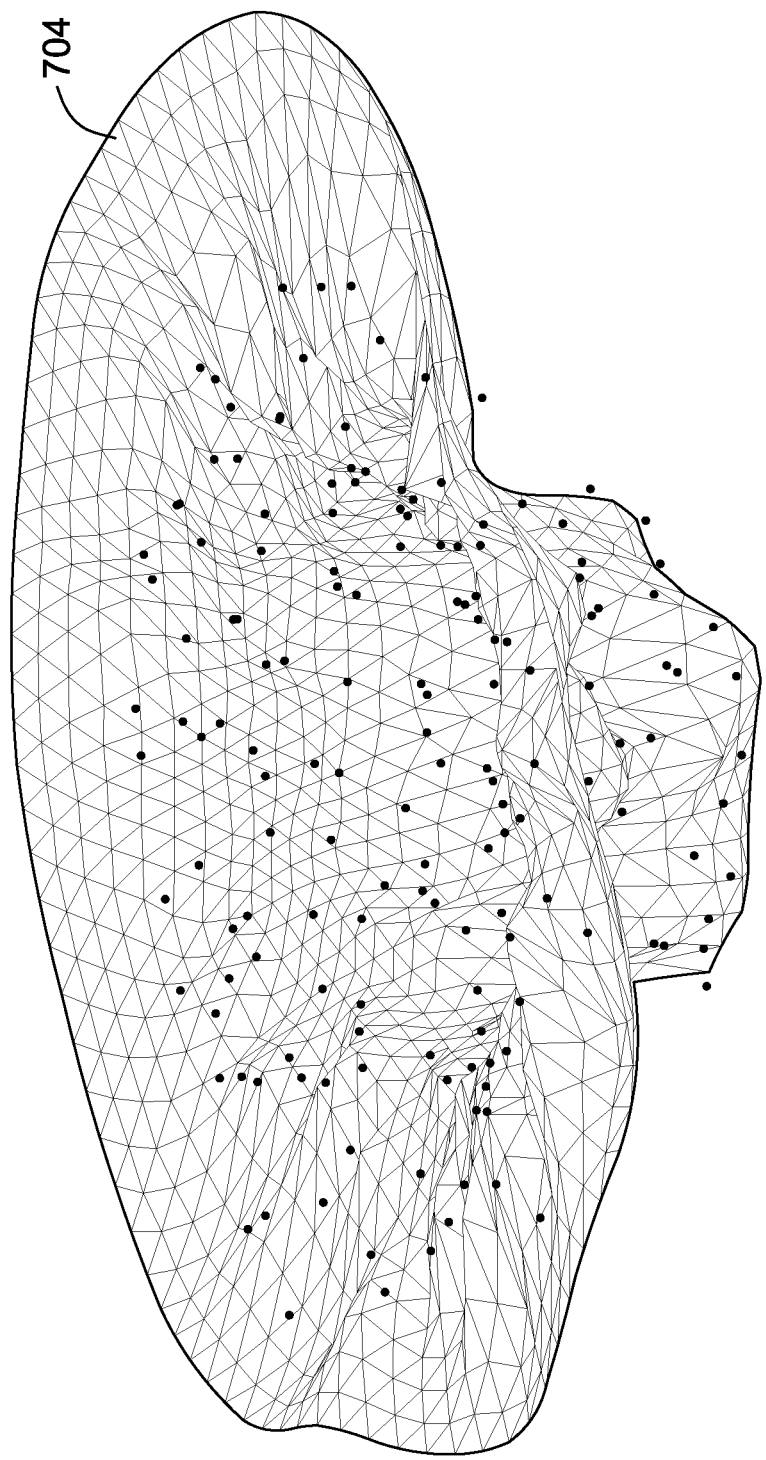
FIG. 7B is a schematic view of a patch surface model generated from the subdivided spherical reference surface illustrated in FIG. 6B.

Subsequent to projecting 508, a thin plate spline function is computed 510 to morph the projected location data points back towards the original location data points. The thin plate spline function may be, for example, a height function that specifies a height value for each vertex on the reference surface. This function is applied to the reference surface to generate a patch surface model. FIG. 7A shows a patch surface model 702 generated from planar reference surface 602 (shown in FIG. 6A), and FIG. 7B shows a patch surface model 704 generated from spherical reference surface 604 (shown in FIG. 6B). In this embodiment, the thin plate spline function is used. Alternatively, any suitable mathematical function may be utilized to generate a patch surface model from the reference surface.

In one embodiment, the thin plate spline function is a three-dimensional radial basis function, in which the projected and original location points are used as fiducial pairs. The thin plate spline function is computed to best morph the projected points onto the original location points, and the transformation is evaluated at each vertex of the reference surface to generate the patch surface model.

To generate a final patch surface model, a boundary is determined 512. The boundary may be determined 512 using a variety of techniques. For example, when the reference surface is a plane or sphere, the boundary may be determined 512 by including any triangle that contains a projected location data point. In another example, when the reference surface is a plane or sphere, a bounding box including all of the projected location data points is defined, and triangles are eroded away from the edges of the bounding box, with the conditions that triangles containing projected location data points cannot be eroded and that no erosion can create a 60° angle (i.e., an isolated triangle protruding or indenting). These conditions facilitate determining 512 a relatively smooth boundary. Alternatively, any suitable erosion algorithm may be used to determine 512 the boundary.

In yet another example, when the reference surface is a plane, the boundary may be determined 512 by generating lines parallel to the edges of the equilateral triangles (which will generate lines at six different orientations) and determining 512 the boundary as the minimal hexagon formed by such lines that includes all of the projected location data points.

In another example, the boundary is determined 512 by stepping around the outer boundary of the reference surface, and for each outer boundary vertex, finding the closest original location data point. If the closest original location data points for two subsequent outer boundary vertices are different, they are connected to form an edge. Once the entire outer boundary has been stepped around, the edges (which form a single closed curve) are projected on the patch surface model, and all triangles and partial triangles outside the single closed curve are trimmed away. This methodology is relatively robust, but may fail when the surface contains a cavity or disjoint components.

In another example, the surface boundary is determined 512 using a method similar to "ball pivoting" (see, e.g., Bernardini, F., et al. 1999, "The ball-pivoting algorithm for surface reconstruction", IEEE Transactions on Visualization and Computer Graphics 5(4): 349-359). In this example, starting from a known exterior location data point, a cylinder is created tangent to the data point, with a predetermined radius and an axis normal to the patch surface model (or normal to a vector between the exterior point and the outer boundary, or some linear combination of the two vectors, etc.). The radius determines how rough or fine the boundary determination is. The cylinder is then "rolled" in a counter-clockwise direction around the surface, projecting each successive location data point touched onto the surface and letting it be part of a closed boundary curve that is trimmed, similar to the previous example. This methodology can handle cavities and multiple components, but is not as robust as the previous example, and may fail if the surface is not smooth (causing the normal vector to vary too quickly).

In yet another example, the user can specify a predetermined "border distance" to remain around the trimmed patch geometry surface. The "border distance" may be adjusted, for example, using a slider displayed on a graphical user interface (GUI). By default, the above procedures leave no border (i.e., zero distance) around the original location data points. But each point in the boundary edge list can simply be moved outward along the patch geometry surface by the user-specified border distance, in the direction of the average normal of its neighboring edges. The moved points can then be used as the new boundary edge list for trimming. Notably, the original "reference surface" of triangles should be large enough to contain the original location data points by at least the border distance. This technique may be used in conjunction with any of the surface boundary determination methods described herein.

Once the boundary is determined 512, the final patch surface model is complete. The final patch surface model may be displayed, for example, on display device 44 (shown in FIG. 1). As will be appreciated by those of skill in the art, diagnostic landmark maps (i.e., maps showing different scalar values for a given characteristic in different colors), tape measures, labels, lesions, cutouts, and/or other markers can be positioned and rendered on the final patch surface model. Of course, as the final patch surface model is not necessarily closed, some objects (e.g., markers and cutouts) may need to be modified accordingly.

Figure 8:
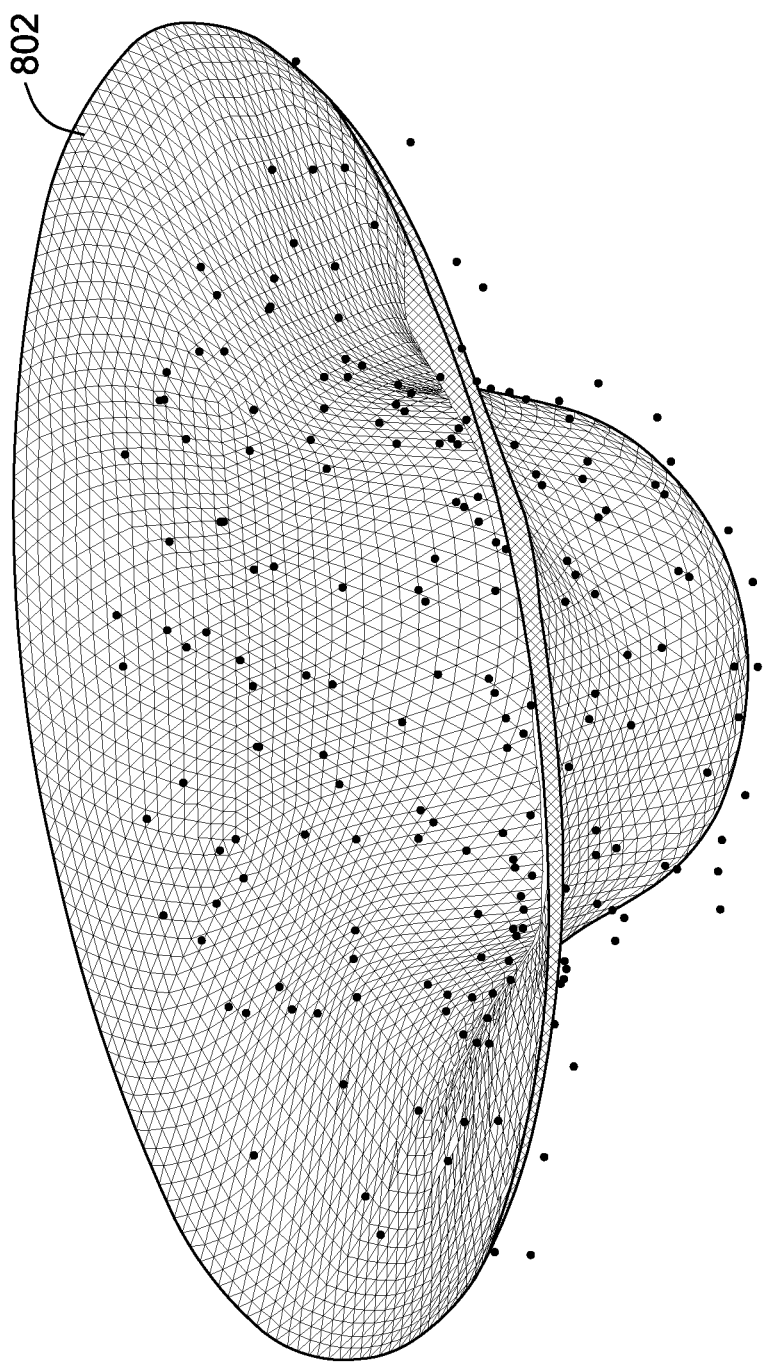
FIG. 8 is a schematic view of a patch surface model generated from the subdivided spherical reference surface illustrated in FIG. 6B, and having a relatively high smoothness coefficient.

In some embodiments, a "smoothness" of the final patch surface model can be selectively adjusted. Specifically, a user can adjust a smoothness coefficient (e.g., by manipulating a slider displayed on display device 44). For a maximum smoothness coefficient, the computed thin plate spline function will generate the reference surface, without any bending or warping. In contrast, for a minimum smoothness coefficient, the computed thin plane spline function will generate a patch surface model that passes through all of the location data points, which may result in a relatively sharp, jagged patch surface model. For purposes of illustration, FIG. 7B shows a patch surface model 704 generated with a relatively low smoothness coefficient selected, and FIG. 8 shows a patch surface model 802 generated with a relatively high smoothness coefficient selected. As shown in FIGS. 7B and 8, surface features are more defined on patch surface model 704 as compared to patch surface model 802. Further, as shown in FIGS. 7B and 8, both patch surface models 704 and 802 are open surface models. In other embodiments, the generated patch surface model may be a closed surface.

It should be understood that model construction system 14, and particularly processing apparatus 16, as described above, may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in some embodiments, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for generating a patch surface model of a geometric structure, the system comprising:
 a computer-based model construction system configured to be coupled to a device that includes at least one sensor configured to acquire a set of original location data points corresponding to respective locations on a surface of the geometric structure, the computer-based model construction system further configured to:
 receive the set of original location data points;
 generate a reference surface based on the set of original location data points, wherein the reference surface is a geometric shape;
 subdivide the reference surface into a plurality of triangles;
 project at least some of the original location data points onto a respective nearest point on the subdivided reference surface;
 compute a function that morphs the projected location data points towards the original location data points;
 transform the reference surface into a patch surface model by applying the function;
 receive a border distance input from a graphical user interface;
 determine a boundary edge for the patch surface model based at least in part on the border distance input and a nearest data point of each point of the original location data points;
 move each of the projected location data points on the boundary edge the border distance input outward along a vector computed as an average normal vector of neighboring edges of the boundary edge; and
 generate the patch surface model for display on a display system.

2. The system of claim 1, wherein the reference surface is one of a plane and a sphere.

3. The system of claim 1, wherein to determine a boundary edge for the patch surface model, the computer-based model construction system is configured to:
for each outer boundary vertex on the patch surface model, determine a closest original location data point;
draw edges between successive closest original location data points to form a closed curve;
project the closed curve onto the patch surface model; and
trim away triangles and partial triangles outside the projected closed curve.

4. The system of claim 1, wherein to determine a boundary edge for the patch surface model, the computer-based model construction system is configured to:
receive an input radius value from a user representing how coarse or fine the boundary is to be computed;
define a cylinder having the input radius value and oriented such that its longitudinal axis is normal to the patch surface model, wherein the cylinder is further defined tangentially to an exterior projected location data point; and
roll the cylinder around the patch surface model to each projected location data point to define a closed boundary curve.

5. The system of claim 1, wherein to compute the function, the computer-based model construction system is further configured to compute a function based on a smoothness coefficient selected by a user.

6. A computer-implemented method of generating a patch surface model of a geometric structure, the method comprising:
generating a set of original location data points corresponding to respective locations on a surface of the geometric structure;
receiving the set of original location data points;
generating a reference surface based on the acquired original location data points, wherein the reference surface is a geometric shape;
subdividing the reference surface into a plurality of triangles;
projecting at least some of the original location data points onto a respective nearest point on the subdivided reference surface;
computing a function that morphs the projected location data points towards the original location data points;
transforming the reference surface into a patch surface model by applying the function;
receiving a border distance input from a graphical user interface;
determining a boundary edge for the patch surface model based at least in part on the border distance input and a nearest data point of each point of the original location data points; and
moving each of the projected location data points on the boundary edge the border distance input outward along a vector computed as an average normal vector of neighboring edges of the boundary edge.

7. The method of claim 6, wherein generating a reference surface comprises generating one of a plane and a sphere.

8. The method of claim 6, wherein subdividing the reference surface into the plurality of triangles comprises subdividing the reference surface into a plurality of equilateral triangles.

9. The method of claim 8, wherein determining the boundary edge for the patch surface model comprises:
for each outer boundary vertex on the patch surface model, determining a closest original location data point;
drawing edges between successive closest original location data points to form a closed curve;
projecting the closed curve onto the patch surface model; and
trimming away triangles and partial triangles outside the projected closed curve.

10. The method of claim 8, wherein determining the boundary edge for the patch surface model comprises:
receiving an input radius value from a user representing how coarse or fine the boundary edge is to be computed;
defining a cylinder having the input radius value and oriented such that its longitudinal axis is normal to the patch surface model, wherein the cylinder is further defined tangentially to an exterior projected location data point; and
rolling the cylinder around the patch surface model to each projected location data point to define a closed boundary curve.

11. The method of claim 6, wherein determining the boundary edge for the patch surface model comprises determining a boundary edge based on a user-specified border distance.

12. The method of claim 6, wherein computing a function comprises computing a based on a smoothness coefficient selected by a user.

13. A processing apparatus for generating a patch surface model of a geometric structure, the processing apparatus configured to:
generate a set of original location data points corresponding to respective locations on a surface of the geometric structure;
receive the set of original location data points;
generate a reference surface based on the acquired original location data points, wherein the reference surface is a geometric shape;
subdivide the reference surface into a plurality of triangles;
project at least some of the original location data points onto a respective nearest point on the subdivided reference surface;
compute a function that morphs the projected location data points towards the original location data points;
transform the reference surface into a patch surface model by applying the function;
receive a border distance input from a graphical user interface;
determine a boundary edge for the patch surface model based at least in part on the border distance input and a nearest data point of each point of the original location data points; and
move each of the projected location data points on the boundary edge the border distance input outward along a vector computed as an average normal vector of neighboring edges of the boundary edge.

14. The processing apparatus of claim 13, wherein to generate the reference surface based on the acquired original location data points, the processing apparatus is configured to generate a plane.

15. The processing apparatus of claim 13, wherein to generate the reference surface based on the acquired original location data points, the processing apparatus is configured to generate a sphere.

16. The processing apparatus of claim 13, wherein to subdivide the reference surface into a plurality of triangles, the processing apparatus is configured to subdivide the reference surface into a plurality of equilateral triangles.

17. The processing apparatus of claim 13, wherein to compute a function, the processing apparatus is configured to compute a function based on a smoothness coefficient selected by a user.

* * * * *